United States Patent [19]

Yonekubo

[11] 3,950,649

[45] Apr. 13, 1976

[54] VERTICAL REFLECTION TYPE FLUORESCENCE MICROPHOTOMETER

[75] Inventor: Ken Yonekubo, Tama, Japan

[73] Assignee: Olympus Optical Co., Ltd., Tokyo, Japan

[22] Filed: Jan. 31, 1975

[21] Appl. No.: 546,185

[30] Foreign Application Priority Data
Feb. 6, 1974 Japan.................................. 49-14503

[52] U.S. Cl................ 250/458; 250/461 B; 356/225
[51] Int. Cl.²............................................ F21K 2/02
[58] Field of Search........ 250/461 B, 458, 459, 361, 250/362, 365, 368; 356/213, 218, 225

[56] References Cited
UNITED STATES PATENTS
3,497,690  2/1970  Wheeless, Jr. et al.......... 250/461 B

*Primary Examiner*—Davis L. Willis
*Attorney, Agent, or Firm*—Haseltine, Lake & Waters

[57] ABSTRACT

Vertical reflection type fluorescence microphotometer in which a specimen under examination is irradiated with an ultraviolet ray directed onto the upper surface of the specimen and light reflected back from the specimen is measured by means of a photoelectric tube. The fluorescence microphotometer comprises a light source for emitting an exciting light, a lens for forming an image of the light source at a position where an aperture diaphragm is located, a relay lens for forming an image of the aperture diaphragm through a dichroic mirror in a focal point located at the image side of an objective lens, and a pinhole arranged between the relay lens and the dichroic mirror. The objective lens can form an image of the pinhole on the upper surface of the specimen as well as an image of the fluorescence emitting position of the specimen through the dichroic mirror at a position where a diaphragm is located. The fluorescence transmitted through the diaphragm is received by the photoelectric tube.

2 Claims, 1 Drawing Figure

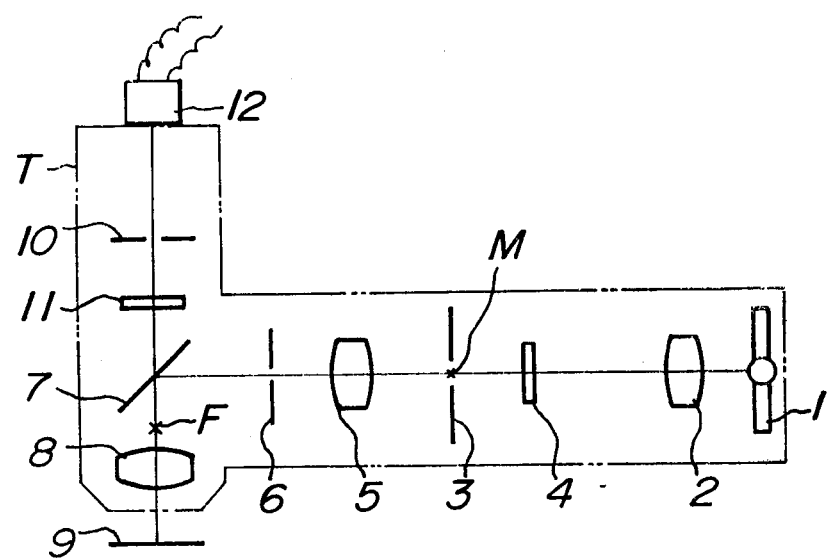

VERTICAL REFLECTION TYPE FLUORESCENCE MICROPHOTOMETER

This invention relates to fluorescence microphotometers and more particularly to a vertical reflection type fluorescence microphotometer.

A transmission light type fluorescence microphotometer has already been proposed. Such transmission light type fluorescence microphotometer makes use of that type of illumination in which a specimen under examination is irradiated with ultraviolet ray directed onto the lower surface of the specimen in order to detect its fluorescence condition. As a result, it is impossible to observe the fluorescence condition on the upper surface of the specimen. Biological tissues and other opaque specimens require, therefore, a special type of illumination with vertical reflected light, in which a specimen under examination is irradiated with ultraviolet ray directed onto the upper surface of the specimen and light reflected back from the specimen is measured.

In the case of observing the fluorescence image of specimens in general, if the specimen is irradiated with exciting light or ultraviolet ray, the specimen becomes self-luminous to form the fluorescence image. But, the fluorescence decays with the lapse of time. Such decay of fluorescence results in an undesirous measurement error of fluorescence microphotometers. In order to avoid such disadvantage, it is preferable to irradiate a small area of the specimen with a spot-like exciting light. The use of such measure makes it possible to reduce the decay of fluorescence with the flare of the fluorescence image decreased and the contrast thereof improved, thereby improving the measurement precision. The invention makes use of a Koana-Naora's illumination system which makes use of a pinhole, aa dichroic mirror, and a diaphragm for the purpose of irradiating the specimen surface with the spot-like exciting light.

In fluorescence microphotometers, it has been common practice to irradiate specimens under examination with an exciting light whose peak is at a given wave length in a range of wave lengths from 350 m$\mu$ to 550 m$\mu$ and measure the intensity of fluorescence produced from the specimen. The difference in wave length between the exciting light and the fluorescence becomes larger than 30 m$\mu$. In addition, the fluorescence has a narrow range of wave lengths and is substantially a monochromatic light. The above described wave length difference larger than 30 m$\mu$ causes troubles in the chromatic aberrations. That is, if the above mentioned Koana-Naora's illumination system is used and the chromatic aberration occurs in the optical system between the pinhole anad the diaphragm, the image of the pinhole could not be precisely formed on the specimen in the case of precisely forming the image of the fluorescence emitting position on the specimen on a position where the diaphragm is located. As a result, there occurs flare and the specimen is not uniformly irradiated with the exciting light to decrease the measurement precision. On the contrary, if the image of the pinhole is caused to be precisely formed on the specimen surface, the precise image of the fluorescence emitting position of the specimen is not formed on the position where the diaphragm is located, thereby degrading the measurement precision.

In order to eliminate the above described chromatic aberration, heretofore, it has been the common practice to insert a lens system for correcting the chromatic aberration between the dichroic mirror and the pinhole. Such lens system for correcting the chromatic aberration, however, must be of a doublet composed of a flint glass lens and a crown glass lens and cemented at their confronting mating faces and hence becomes complex in construction. In addition, the flint glass and cementing agent when irradiated with the exciting light become self-luminous to produce the fluorescence, and as a result, the flare is produced thereby degrading the measurement precision. Moreover, some lens is liable to decrease the light transmission, thereby degrading the measurement precision.

An object of the invention is to provide a vertical reflection type fluorescence microphotometer which makes use of a Koana-Naora's illumination system in order to eliminate decay of fluorescence with the lapse of time and which is so constructed that the above described measurement error due to the chromatic aberration can be obviated.

A feature of the invention is the provision of a vertical reflection type fluorescence microphotometer which comprises a light source for emitting an exciting light, a lens for forming an image of the light source at a position where an aperture diaphragm is located, a relay lens for forming an image of said aperture diaphragm through a dichroic mirror in a focal point located at the image side of an objective lens, and a pinhole arranged between the relay lens and the dichroic mirror.

As a result the objective lens not only can form an image of the pinhole on the upper surface of the specimen but also can form an image of fluorescence emitting position of the specimen through the dichroic mirror at a position where a diaphragm is located and the fluorescence transmitted through said diaphragm is received by a photoelectric tube.

The invention will now be described in greater detail with reference to the accompanying drawing, of which the sole FIGURE schematically illustrates a vertical reflection type fluorescence microphototmeter according to the invention.

The vertical reflection type fluorescence microphotometer comprises an exciting light source 1 and a lens 2 which serves to form an image M of the light source 1 at a position where an aperture diaphragm 3 is located. Between the lens 2 and the aperture diaphragm 3 is arranged an exciting light pass filter 4. Spaced rearwardly from the aperture diaphragm 3 are a relay lens 5, a pinhole 6 and a dichroic mirror 7. Between the dichroic mirror 7 and a specimen 9 under examination is arranged an objective lens 8.

The relay lens 5 serves to form the light source image M formed at the aperture diaphragm 3 through the pinhole 6 at a focal position F at the rear of the objective lens 8. The pinhole 6 can act as a diaphragm for field of view. The objective lens 8 serves to form image of the pinhole 6 through the dichroic mirror 7 on the upper surface of the specimen 9.

In the present invention, the dichroic mirror 7 has a property of reflecting the exciting light and transmitting the fluorescence therethrough.

Spaced upwardly from the dichroic mirror 7 are an exciting light cut filter 11, a diaphragm 10 and a photoelectric cell 12. The objective lens 8 also serves to form the image of the fluorescence emitting position of the specimen 9 through the dichroic mirror 7 at a position where the diaphragm 10 is located. The photoelectric tube 12 is disposed outside a microscope tube T and when exposed to the fluorescence generates an electric signal which is supplied through an electronic amplifier to a galvanometer which indicates intensity of the fluorescence in the usual way. The electronic amplifier and the galvanometer are omitted for ease of illustration.

As explained hereinbefore, the use of the measures described, that the objective lens 8 can form the image of the pinhole 6 on the upper surface of the specimen 9, ensures a simplification of the microphotometer to an extent that it is sufficient to dispose only the objective lens 8 between the pinhole 6 and the specimen 9.

In general, the objective lens 8 has a high degree of correction for all visual regions from the near ultraviolet region, and as a result, the image of the pinhole 6 is precisely formed on the upper surface of the specimen 9, and the image of the fluorescence emitting position of the specimen 9 is precisely formed on the position of the diaphragm 10. In addition, the objective lens 8 does not decrease the transmission of the exciting light when it is irradiated therewith.

What is claimed is:

1. A vertical reflection-type fluorescence microphotometer, comprising: an optical illumination system; an optical photometric system and a dichroic mirror for reflecting an optical axis of said illumination system and aligning the reflected optical axis with an optical axis of said photometric system; said illumination system including an exciting light source, a lens for forming an image of said light source, an aperture diaphragm arranged at a position where said image of the light source is formed, a relay lens arranged between said diaphragm and said mirror, and a pinhole arranged between said relay lens and said mirror; said photometric system including an objective lens between said mirror and specimen for forming an image of said pinhole, reflected by said mirror on the upper surface of the specimen, said relay lens forming an image of said aperture diaphragm at a focal position at the rear of said objective lens; a diaphragm arranged at a position where a fluorescent image of the specimen is formed by said objective lens; and a photoelectric tube for receiving the fluorescence transmitted through said last-named diaphragm.

2. The microphotometer as defined in claim 1, wherein said illumination system further includes an exciting light-pass filter arranged between said lens thereof and said aperture diaphragm.

* * * * *